(12) United States Patent
Bonnette et al.

(10) Patent No.: US 8,162,878 B2
(45) Date of Patent: Apr. 24, 2012

(54) EXHAUST-PRESSURE-OPERATED BALLOON CATHETER SYSTEM

(75) Inventors: Michael John Bonnette, Minneapolis, MN (US); Eric Joel Thor, Arden Hills, MN (US); Douglas James Ball, Coon Rapids, MN (US); Debra M. Kozak, Forest Lake, MN (US)

(73) Assignee: MEDRAD, Inc., Indianola, PA (US)

( * ) Notice: Subject to any disclaimer, the term of this patent is extended or adjusted under 35 U.S.C. 154(b) by 238 days.

(21) Appl. No.: 11/294,006

(22) Filed: Dec. 5, 2005

(65) Prior Publication Data

US 2009/0149807 A1 Jun. 11, 2009

(51) Int. Cl.
*A61M 29/00* (2006.01)
*A61M 31/00* (2006.01)
*A61B 17/22* (2006.01)

(52) U.S. Cl. ............... 604/98.01; 606/159; 606/194; 604/509

(58) Field of Classification Search ............ 604/96.01, 604/97.01, 97.02, 97.03, 98.01, 99.01, 100.01–100.03, 604/101.01
See application file for complete search history.

(56) References Cited

U.S. PATENT DOCUMENTS

| | | | |
|---|---|---|---|
| 3,435,826 A * | 4/1969 | Fogarty | 606/194 |
| 3,695,208 A | 10/1972 | Fixler | |
| 3,752,617 A | 8/1973 | Burlis et al. | |
| 3,833,003 A * | 9/1974 | Taricco | 604/509 |
| 3,930,505 A | 1/1976 | Wallach | |
| 4,100,246 A | 7/1978 | Frisch | |
| 4,168,709 A | 9/1979 | Bentov | |
| 4,224,943 A | 9/1980 | Johnson et al. | |
| 4,248,234 A | 2/1981 | Assenza et al. | |
| 4,290,428 A | 9/1981 | Durand et al. | |
| 4,328,811 A | 5/1982 | Fogarty | |
| 4,385,635 A | 5/1983 | Ruiz | |
| 4,515,592 A | 5/1985 | Frankhouser | |
| 4,535,757 A * | 8/1985 | Webster, Jr. | 600/18 |
| 4,610,662 A | 9/1986 | Weikl et al. | |
| 4,631,052 A | 12/1986 | Kensey | |

(Continued)

FOREIGN PATENT DOCUMENTS

DE 3421390 A1 12/1985

(Continued)

OTHER PUBLICATIONS

International Search Report from corresponding International Application PCT/US08/87422, Feb. 12, 2009.

(Continued)

*Primary Examiner* — Kevin C Sirmons
*Assistant Examiner* — William Carpenter
(74) *Attorney, Agent, or Firm* — David Schramm

(57) ABSTRACT

An exhaust-pressure-operated balloon catheter system which is a cross stream thrombectomy catheter, such as, but not limited to, an Angiojet® catheter with a flexible and expandable balloon, wherein the balloon is formed from and is continuous with the catheter tube which, in part, forms the cross stream thrombectomy catheter, wherein the balloon is deployable and expandable about the distal region of the cross stream thrombectomy catheter to act as an occluder device, and wherein the balloon is located proximal to the fluid jet emanator and inflow and outflow orifices upstream of ablative cross stream flows. The balloon is expandably deployed by the exhaust or back pressure created by the operation of the cross stream flows as generated by the fluid jets of the operating exhaust-pressure-operated balloon catheter system.

19 Claims, 8 Drawing Sheets

U.S. PATENT DOCUMENTS

| | | | |
|---|---|---|---|
| 4,636,346 A | 1/1987 | Gold et al. | |
| 4,690,672 A | 9/1987 | Veltrup | |
| 4,739,768 A | 4/1988 | Engelson | |
| 4,747,405 A | 5/1988 | Leckrone | |
| 4,781,186 A | 11/1988 | Simpson et al. | |
| 4,782,834 A | 11/1988 | Maguire et al. | |
| 4,790,813 A | 12/1988 | Kensey | |
| 4,834,710 A | 5/1989 | Fleck | |
| 4,842,579 A | 6/1989 | Shiber | |
| 4,883,459 A | 11/1989 | Calderon | |
| 4,888,146 A | 12/1989 | Dandeneau | |
| 4,898,574 A | 2/1990 | Uchiyama et al. | |
| 4,898,591 A | 2/1990 | Jang et al. | |
| 4,902,276 A | 2/1990 | Zakko | |
| 4,913,698 A | 4/1990 | Ito et al. | |
| 4,917,667 A * | 4/1990 | Jackson | 604/103 |
| 4,950,238 A | 8/1990 | Sullivan | |
| 5,011,469 A | 4/1991 | Buckberg et al. | |
| 5,015,232 A | 5/1991 | Maglinte | |
| 5,042,976 A * | 8/1991 | Ishitsu et al. | 604/96.01 |
| 5,085,549 A | 2/1992 | Londry | |
| 5,085,635 A | 2/1992 | Cragg | |
| 5,085,649 A | 2/1992 | Flynn | |
| 5,086,842 A | 2/1992 | Cholet | |
| 5,090,960 A | 2/1992 | Don Michael | |
| 5,092,873 A | 3/1992 | Simpson et al. | |
| 5,114,399 A | 5/1992 | Kovalcheck | |
| 5,135,482 A | 8/1992 | Neracher | |
| 5,163,431 A | 11/1992 | Griep | |
| 5,171,221 A | 12/1992 | Samson | |
| 5,215,614 A | 6/1993 | Wijkamp | |
| 5,221,270 A | 6/1993 | Parker | |
| 5,222,941 A | 6/1993 | Don Michael | |
| 5,234,416 A | 8/1993 | Macaulay et al. | |
| 5,242,395 A | 9/1993 | Maglinte | |
| 5,250,034 A | 10/1993 | Appling et al. | |
| 5,250,059 A | 10/1993 | Andreas et al. | |
| 5,254,107 A | 10/1993 | Soltesz | |
| 5,259,842 A | 11/1993 | Plechinger et al. | |
| 5,267,979 A | 12/1993 | Appling et al. | |
| 5,273,526 A | 12/1993 | Dance et al. | |
| 5,300,022 A | 4/1994 | Klapper et al. | |
| 5,306,249 A | 4/1994 | Don Michael | |
| 5,308,342 A | 5/1994 | Sepetka et al. | |
| RE34,633 E | 6/1994 | Sos et al. | |
| 5,318,518 A | 6/1994 | Plechinger et al. | |
| 5,320,599 A | 6/1994 | Griep et al. | |
| 5,324,285 A | 6/1994 | Cannon | |
| 5,331,679 A | 7/1994 | Hirukawa | |
| 5,342,386 A | 8/1994 | Trotta | |
| 5,356,388 A | 10/1994 | Sepetka et al. | |
| 5,358,485 A | 10/1994 | Vance et al. | |
| 5,360,379 A | 11/1994 | Carelli et al. | |
| 5,370,609 A | 12/1994 | Drasler et al. | |
| 5,372,601 A | 12/1994 | Lary | |
| 5,380,307 A | 1/1995 | Chee et al. | |
| 5,385,548 A * | 1/1995 | Williams et al. | 604/102.02 |
| 5,399,164 A | 3/1995 | Snoke et al. | |
| 5,409,454 A | 4/1995 | Fischell et al. | |
| 5,425,723 A | 6/1995 | Wang | |
| 5,456,665 A | 10/1995 | Postell et al. | |
| 5,456,674 A | 10/1995 | Bos et al. | |
| 5,478,330 A | 12/1995 | Imran et al. | |
| 5,492,532 A | 2/1996 | Ryan et al. | |
| 5,496,267 A | 3/1996 | Drasler et al. | |
| 5,496,294 A | 3/1996 | Hergenrother et al. | |
| 5,499,973 A | 3/1996 | Saab | |
| 5,513,956 A | 5/1996 | Lewis et al. | |
| 5,514,092 A | 5/1996 | Forman et al. | |
| 5,531,679 A | 7/1996 | Schulman et al. | |
| 5,531,685 A | 7/1996 | Hemmer et al. | |
| 5,536,242 A | 7/1996 | Willard et al. | |
| 5,542,924 A | 8/1996 | Snoke et al. | |
| 5,554,121 A | 9/1996 | Ainsworth et al. | |
| 5,558,642 A | 9/1996 | Schweich, Jr. et al. | |
| 5,571,094 A | 11/1996 | Sirhan | |
| 5,599,299 A | 2/1997 | Weaver et al. | |
| 5,599,325 A | 2/1997 | Ju et al. | |
| 5,609,574 A | 3/1997 | Kaplan et al. | |
| 5,624,397 A | 4/1997 | Snoke et al. | |
| 5,628,730 A | 5/1997 | Shapland et al. | |
| 5,634,897 A | 6/1997 | Dance et al. | |
| 5,643,279 A | 7/1997 | Trotta | |
| 5,658,263 A | 8/1997 | Dang et al. | |
| 5,662,608 A * | 9/1997 | Imran et al. | 604/103.07 |
| 5,662,622 A | 9/1997 | Gore et al. | |
| 5,668,702 A | 9/1997 | Nassimi | |
| 5,676,659 A | 10/1997 | McGurk | |
| 5,681,336 A | 10/1997 | Clement et al. | |
| 5,683,345 A | 11/1997 | Waksman et al. | |
| 5,687,714 A | 11/1997 | Kolobow et al. | |
| 5,702,439 A | 12/1997 | Keith et al. | |
| 5,704,926 A | 1/1998 | Sutton | |
| 5,713,849 A | 2/1998 | Bosma et al. | |
| 5,769,828 A | 6/1998 | Jonkman | |
| 5,792,167 A | 8/1998 | Kablik et al. | |
| 5,795,322 A | 8/1998 | Boudewijn | |
| 5,795,325 A | 8/1998 | Valley et al. | |
| 5,817,046 A | 10/1998 | Glickman | |
| 5,843,022 A | 12/1998 | Willard et al. | |
| 5,900,444 A | 5/1999 | Zamore | |
| 5,906,590 A | 5/1999 | Hunjan et al. | |
| 5,919,163 A | 7/1999 | Glickman | |
| 5,928,181 A | 7/1999 | Coleman et al. | |
| 5,929,633 A | 7/1999 | Fischer | |
| 5,935,501 A | 8/1999 | Andrews et al. | |
| 5,944,686 A | 8/1999 | Patterson et al. | |
| 5,951,513 A * | 9/1999 | Miraki | 604/96.01 |
| 5,957,901 A | 9/1999 | Mottola et al. | |
| 5,989,210 A | 11/1999 | Morris et al. | |
| 5,989,271 A | 11/1999 | Bonnette | |
| 6,001,078 A | 12/1999 | Reekers | |
| 6,004,269 A | 12/1999 | Crowley et al. | |
| 6,004,339 A | 12/1999 | Wijay | |
| 6,022,336 A | 2/2000 | Zadno-Azizi et al. | |
| 6,024,729 A | 2/2000 | Dehdashtian et al. | |
| 6,027,499 A | 2/2000 | Johnston et al. | |
| 6,044,845 A | 4/2000 | Lewis | |
| 6,062,623 A | 5/2000 | Lemmen | |
| 6,063,069 A | 5/2000 | Cragg et al. | |
| 6,068,623 A | 5/2000 | Zadno-Azizi et al. | |
| 6,074,374 A | 6/2000 | Fulton | |
| 6,096,001 A | 8/2000 | Drasler et al. | |
| 6,099,496 A | 8/2000 | Berthiaume et al. | |
| 6,106,642 A | 8/2000 | DiCarlo et al. | |
| 6,129,697 A | 10/2000 | Drasler et al. | |
| 6,129,698 A | 10/2000 | Beck | |
| 6,135,977 A | 10/2000 | Drasler et al. | |
| 6,165,199 A | 12/2000 | Barbut | |
| 6,179,816 B1 | 1/2001 | Mottola et al. | |
| RE37,153 E | 5/2001 | Henszey et al. | |
| 6,224,570 B1 | 5/2001 | Le et al. | |
| 6,241,744 B1 | 6/2001 | Imran et al. | |
| 6,258,061 B1 | 7/2001 | Drasler et al. | |
| 6,273,880 B1 | 8/2001 | Berg et al. | |
| 6,283,950 B1 | 9/2001 | Appling | |
| 6,331,176 B1 * | 12/2001 | Becker et al. | 604/533 |
| 6,395,208 B1 | 5/2002 | Herweck et al. | |
| 6,524,300 B2 | 2/2003 | Meglin | |
| 6,533,782 B2 | 3/2003 | Howell et al. | |
| 6,544,220 B2 | 4/2003 | Shuman et al. | |
| 6,592,549 B2 | 7/2003 | Gerdts et al. | |
| 6,596,818 B1 | 7/2003 | Zamore | |
| 6,652,548 B2 | 11/2003 | Evans et al. | |
| 6,656,550 B1 * | 12/2003 | Zamore | 428/35.7 |
| 6,676,637 B1 | 1/2004 | Bonnette et al. | |
| 6,749,583 B2 * | 6/2004 | Briscoe et al. | 604/96.01 |
| 6,755,803 B1 * | 6/2004 | Le et al. | 604/22 |
| 6,773,452 B2 | 8/2004 | Shaker | |
| 6,790,196 B2 | 9/2004 | Kokate et al. | |
| 6,834,842 B2 | 12/2004 | Houde | |
| 6,875,193 B1 * | 4/2005 | Bonnette et al. | 604/22 |
| 6,926,726 B2 | 8/2005 | Drasler et al. | |
| 6,929,633 B2 | 8/2005 | Evans et al. | |
| 6,939,320 B2 * | 9/2005 | Lennox | 604/103.02 |
| 6,942,635 B2 | 9/2005 | Rosenblatt et al. | |
| 6,945,951 B1 * | 9/2005 | Bonnette et al. | 604/22 |

| | | |
|---|---|---|
| 7,033,776 B2 | 4/2006 | Toombs |
| 7,131,981 B2 | 11/2006 | Appling et al. |
| 7,163,533 B2 | 1/2007 | Hobbs et al. |
| 7,182,756 B2 | 2/2007 | Saeed et al. |
| 7,220,269 B1 | 5/2007 | Ansel et al. |
| 7,226,433 B2 | 6/2007 | Bonnette et al. |
| 7,314,461 B2 | 1/2008 | Carter et al. |
| 7,369,358 B2 | 5/2008 | Edelman et al. |
| 7,374,560 B2 | 5/2008 | Ressemann et al. |
| 7,396,358 B2 | 7/2008 | Appling et al. |
| 7,399,307 B2 | 7/2008 | Evans et al. |
| 7,422,579 B2 | 9/2008 | Wahr et al. |
| 2001/0051785 A1 | 12/2001 | Bonnette et al. |
| 2001/0051811 A1 | 12/2001 | Bonnette et al. |
| 2001/0053920 A1 | 12/2001 | Shaker |
| 2001/0056257 A1* | 12/2001 | Drasler et al. ............ 604/96.01 |
| 2002/0032408 A1 | 3/2002 | Parker et al. |
| 2002/0049423 A1 | 4/2002 | Howell et al. |
| 2002/0068895 A1 | 6/2002 | Beck |
| 2002/0077594 A1 | 6/2002 | Chien et al. |
| 2002/0120226 A1 | 8/2002 | Beck |
| 2002/0188276 A1 | 12/2002 | Evans et al. |
| 2003/0069541 A1 | 4/2003 | Gillis et al. |
| 2003/0088194 A1 | 5/2003 | Bonnette et al. |
| 2003/0139751 A1 | 7/2003 | Evans et al. |
| 2003/0195490 A1 | 10/2003 | Boatman et al. |
| 2004/0006306 A1 | 1/2004 | Evans et al. |
| 2004/0019323 A1 | 1/2004 | Carter et al. |
| 2004/0039306 A1 | 2/2004 | Eberhart et al. |
| 2004/0068248 A1 | 4/2004 | Mooney et al. |
| 2004/0093008 A1 | 5/2004 | Zamore |
| 2004/0193196 A1 | 9/2004 | Appling et al. |
| 2004/0210194 A1 | 10/2004 | Bonnette et al. |
| 2005/0049574 A1 | 3/2005 | Petrick et al. |
| 2005/0059957 A1 | 3/2005 | Campbell et al. |
| 2005/0107738 A1 | 5/2005 | Slater et al. |
| 2006/0064123 A1 | 3/2006 | Bonnette et al. |
| 2008/0275393 A1 | 11/2008 | Bonnette |

FOREIGN PATENT DOCUMENTS

| | | |
|---|---|---|
| DE | 3705339 A1 | 9/1988 |
| EP | 0232678 A2 | 8/1987 |
| EP | 0251512 A1 | 1/1988 |
| EP | 0528181 A1 | 2/1993 |
| EP | 1382366 A1 | 1/2004 |
| GB | 1571459 A | 7/1980 |
| WO | 9005493 A1 | 5/1990 |
| WO | 9410917 A1 | 5/1994 |
| WO | 9510232 A1 | 4/1995 |
| WO | WO2007067661 | 6/2007 |

OTHER PUBLICATIONS

International Search Report from corresponding International Application PCT/US08/87109, Feb. 11, 2009.

Final Rejection from corresponding U.S. Appl. No. 11/294,006, Aug. 6, 2008.

International Search Report from corresponding International Application PCT/US06/46621, Nov. 10, 2008.

* cited by examiner

EXHAUST-PRESSURE-OPERATED BALLOON CATHETER SYSTEM

CROSS REFERENCES TO RELATED APPLICATIONS

This patent application is related to application Ser. No. 10/455,096 entitled "Thrombectomy Catheter Device Having a Self-Sealing Hemostasic Valve" filed on Jun. 05, 2003, which is pending.

BACKGROUND OF THE INVENTION

1. Field of the Invention

The present invention relates to a thrombectomy catheter, and more particularly, relates to an exhaust-pressure-operated balloon catheter system which is a cross stream thrombectomy catheter, such as, but not limited to, an Angiojet® catheter with a flexible and expandable balloon, wherein the balloon is deployable and expandable about the distal region of the cross stream thrombectomy catheter and wherein the balloon is located proximal to the fluid jet emanator and inflow and outflow orifices upstream of ablative cross stream flows. The balloon is expandably deployed by the exhaust or back pressure created by the operation of the cross stream flows as generated by the fluid jets of the operating exhaust-pressure-operated balloon catheter system.

2. Description of the Prior Art

Prior art thrombectomy catheter systems incorporated a manifold and a catheter having a plurality of inflow and outflow orifices involved with ablation jet flow in cooperation with an inflatable occludive balloon. The occlusive balloons, for the most, required elaborate schemes for attachment to the catheter tube which acted as an exhaust tube to carry away particulate and other fluids present in the ablation processes. Often, the balloon would be aligned over and about the catheter/exhaust tube and then secured thereto by adhesive, electronic bonding, or the like. A separate inflation lumen including inflation orifices was often required for communication with and for inflation of the occlusive balloon; or complex schemes requiring the use of moveable components were relied on to expand the occlusive balloon during the thrombectomy procedure. Other expansion methods were used as well.

SUMMARY OF THE INVENTION

The general purpose of the present invention is to provide an exhaust-pressure-operated balloon catheter system to elegantly stop blood flow in a vessel. Flow cessation optimizes the effectivity of Angiojet® style thrombectomy catheter devices and procedures involving drug infusion, embolization containment, thrombectomy and other procedures, and reduces hemolysis since the amount of blood available to lyse is minimized. This invention utilizes a proximally located balloon with an Angiojet® thrombectomy catheter device involving cross stream ablation flows, and, more specifically, utilizes an inflatable balloon formed out of the catheter tube (exhaust tube) of an Angiojet® thrombectomy catheter device which is proximally located with respect to cross stream flows and deployed using the back pressure created by the operation of the cross stream flows generated by the fluid jets of the thrombectomy catheter. Although balloons attached to catheters proximal or distal to the inflow and outflow orifices have been suggested in the past, the present invention goes one step further by creating a balloon incorporating the structure of a catheter tube (exhaust tube) of Pebax, polyurethane or other suitable material while using the exhaust pressure of the fluid jets to fill and sustain expansion of the balloon for purposes of proximal protection or occlusion, and in some cases when used in antigrade flow, distal protection. This arrangement minimizes overall general profile, minimizes the number of components and design complexity, minimizes manufacturing cost, and provides an exhaust-pressure-operated balloon catheter system which is very easy to use since the balloon is deployed automatically when the exhaust-pressure-operated balloon catheter system is activated.

Since Angiojet® style thrombectomy catheters remove debris more effectively in stagnant flow, as well as being more effective in other procedures having a stagnant flow, the present invention is useful in several applications. The invention could be used in cooperation with a filter to more effectively remove debris from within and around the filter. The invention could be used to increase the amount of debris/thrombus removed from a particular vessel length. With this in mind, the invention could also minimize any distal or proximal embolization. The invention could be used to deliver drugs more effectively to a stagnant field. The balloon could also be used for centering or positioning a catheter in a vessel. Finally, the invention could be used to break up clots as it is moved through a blocked vessel (modified embolectomy).

According to one or more embodiments of the present invention, there is provided an exhaust-pressure-operated balloon catheter system including a manifold and closely associated components, including a hemostatic nut assembly, a self-sealing hemostatic valve, a threaded high pressure connection port, a catheter tube (sometimes referred to as an exhaust tube) connectingly extending from the manifold through a strain relief, a catheter tube tapered tip having a plurality of outflow orifices and inflow orifices in close proximity thereto extending through the sidewalls of the catheter tube, a high pressure tube connectively extending from the threaded high pressure connection port through the manifold and through the catheter tube to a fluid jet emanator located distal to the plurality of outflow orifices and inflow orifices, a first set of support rings spaced along and secured to a distal portion of the high pressure tube, a support ring and the previously mentioned fluid jet emanator spaced along and secured to a distal portion of the high pressure tube, a thin wall section of the catheter tube (herein referred to as the balloon) aligned between the full thickness catheter portions, wherein the full thickness catheter portions align over and about, as well as extending in opposite directions from, the first set of spaced support rings, radiopaque marker bands secured over and about the catheter tube in alignment with the underlying first set of support rings, and a portion of the catheter tube which is in close proximity to the plurality of outflow orifices and inflow orifices, wherein such a portion of the catheter tube aligns over and about the spaced support ring and the previously mentioned fluid jet emanator and is secured thereabout and thereto by radiopaque marker bands.

One significant aspect and feature of the exhaust-pressure-operated balloon catheter system, the present invention, is the use of a proximally located balloon (herein called the proximal balloon) on an Angiojet® style thrombectomy catheter, wherein the balloon is of decreased wall thickness and is created from the catheter tube (exhaust tube) itself.

Another significant aspect and feature of the exhaust-pressure-operated balloon catheter system is a proximal balloon on an Angiojet® thrombectomy catheter which is deployed by the back pressure created by operating the exhaust-pressure-operated balloon catheter system.

Another significant aspect and feature of the exhaust-pressure-operated balloon catheter system is a proximal balloon on an Angiojet® thrombectomy catheter which is fixed and positioned between two marker bands with underlying support rings or by other suitable means.

Another significant aspect and feature of the exhaust-pressure-operated balloon catheter system is a proximal balloon on an Angiojet® thrombectomy catheter used for the purpose of cessation of fluid flow in a blood vessel or other body conduit.

Another significant aspect and feature of the exhaust-pressure-operated balloon catheter system is a proximal balloon on an Angiojet® thrombectomy catheter used for the purpose of cessation of fluid flow in a blood vessel or other body conduit to maximize the effect of the thrombectomy catheter in terms of debris or tissue removal.

Another significant aspect and feature of the exhaust-pressure-operated balloon catheter system is a proximal balloon on an Angiojet® thrombectomy catheter used for the purpose of cessation of fluid flow in a blood vessel or other body conduit to maximize the effect of the thrombectomy catheter in terms of debris or tissue removal from a distal protection filter wire or a balloon.

Another significant aspect and feature of the exhaust-pressure-operated balloon catheter system is a proximal balloon on an Angiojet® thrombectomy catheter used for the purpose of centering a catheter tube.

Another significant aspect and feature of the exhaust-pressure-operated balloon catheter system is a proximal balloon on an Angiojet® thrombectomy catheter used for the purpose of modified embolectomy.

Another significant aspect and feature of the exhaust-pressure-operated balloon catheter system is for the purpose of drug delivery to a blood vessel or other body conduit.

Having thus briefly described an embodiment of the present invention and having mentioned some significant aspects and features of the present invention, it is the principal object of the present invention to provide an exhaust-pressure-operated balloon catheter system.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENT

Figure 1:
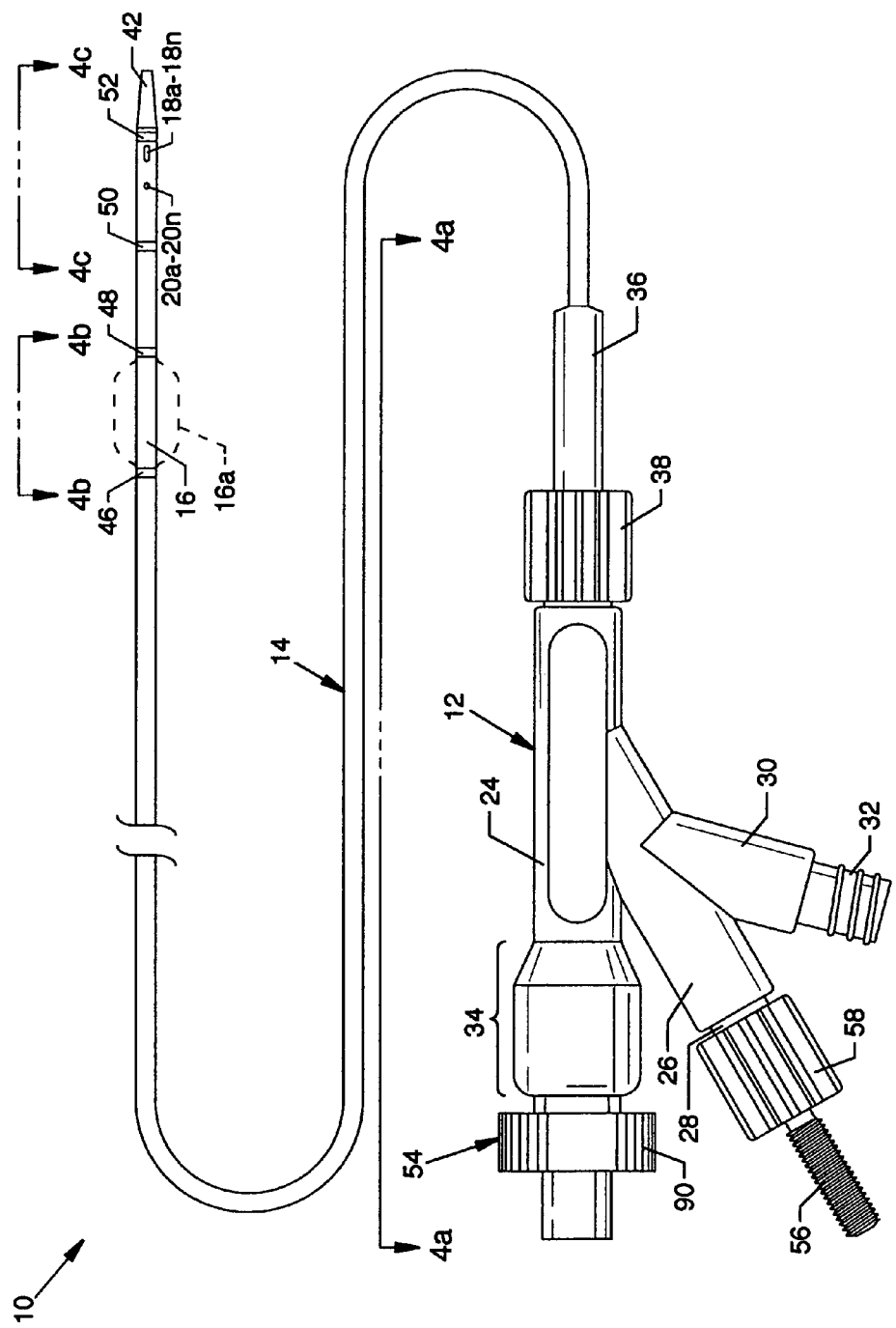
FIG. 1 is a plan view showing the visible components of an exhaust-pressure-operated balloon catheter system, the present invention, illustrating major features, components or assemblies of the invention.

FIG. 1 is a plan view showing the visible components of an exhaust-pressure-operated balloon catheter system 10, the present invention, illustrating major features, components or assemblies of the invention. Such major features, components or assemblies of the invention include a one-piece manifold 12 having a catheter tube 14 extending therefrom and attached thereto, including details as now described. A flexible, expandable and inflatable balloon, herein referred to as the balloon 16, is shown in the deflated position being an integral part of the catheter tube 14, the latter of which can be referred to as an exhaust tube. The balloon 16 is located near the distal end of the catheter tube 14 just proximal to a plurality of inflow orifices 18a-18n and a plurality of outflow orifices 20a-20n located along and about the distal end of the catheter tube 14. The expanded profile of the balloon 16 is shown in dashed lines as an expanded balloon 16a. The visible portion of the one-piece manifold 12 includes a central tubular body 24, a high pressure branch 26 including an integral threaded connector port 28 (FIG. 2) extending angularly from the central tubular body 24, an exhaust branch 30 including an integral threaded connector port 32 extending angularly from the high pressure connection branch 26, and a cavity body 34 extending proximally from the central tubular body 24. The catheter tube 14 has a lumen 40 (FIG. 2) and the proximal end of the catheter tube 14 extends through and seals against the interior of a strain relief 36 and through a concentrically located connector 38 such that the lumen 40 communicates with the interior of the manifold 12. The catheter tube 14 extends distally to include a tapered tip 42 whereat the lumen 40 decreases in diameter (see FIG. 4c) and wherein all parts are flexible. Opposed radiopaque marker bands 46 and 48 are shown located around and about the catheter tube 14 at both sides of the balloon 16, and opposed radiopaque marker bands 50 and 52 are shown located around and about the catheter tube 14 at both sides of the plurality of inflow orifices 18a-18n and the plurality of outflow orifices 20a-20n. A hemostatic nut assembly 54 aligns to and snappingly and threadingly engages features of the cavity body 34. A threaded high pressure connection port 56 suitably secures to the inner portion of the integral threaded connector port 28 of the high pressure connection branch 26 in cooperation with a connector 58.

Figure 2:
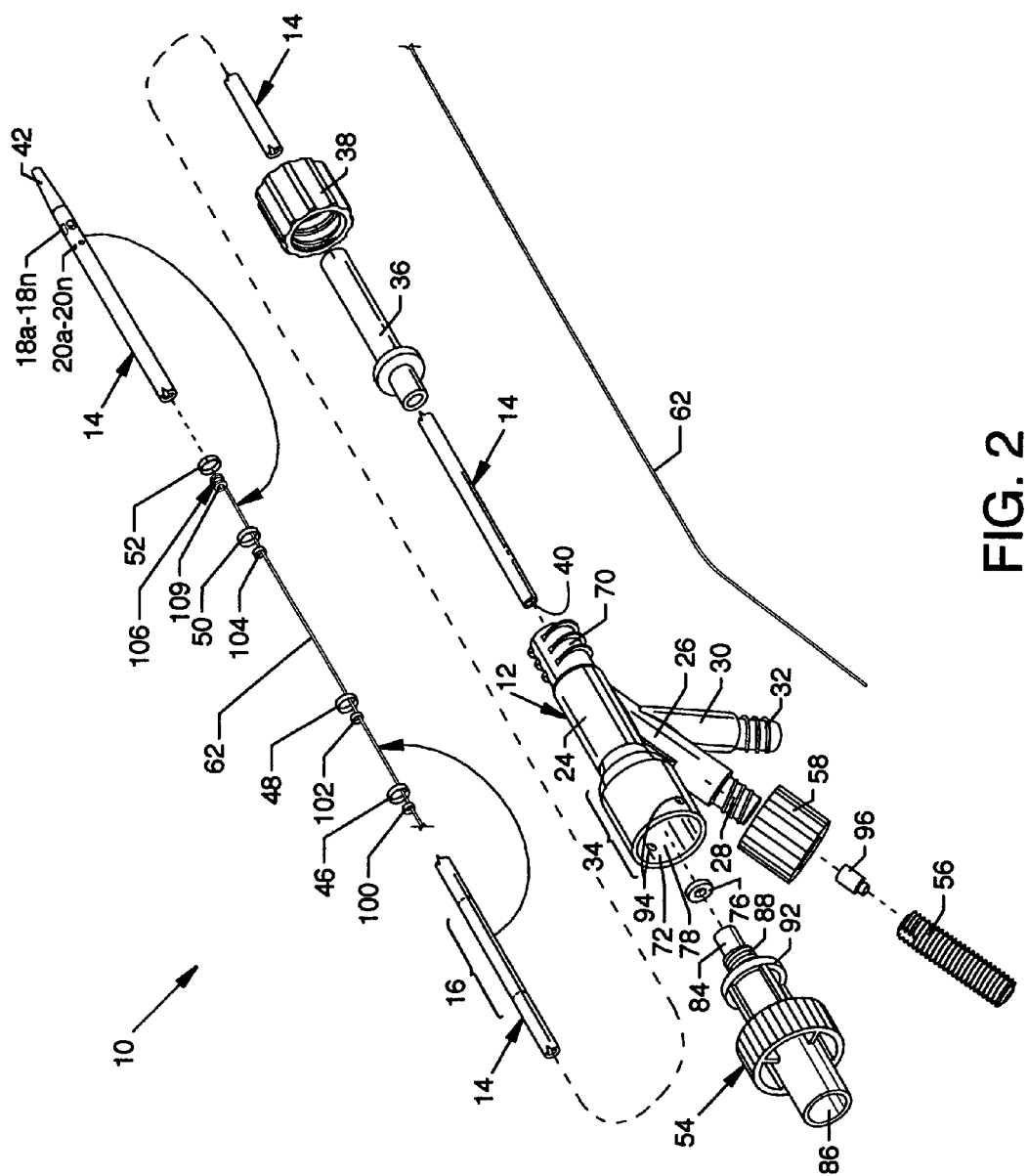
FIG. 2 is a segmented exploded isometric view of the exhaust-pressure-operated balloon catheter system.
Figure 3:
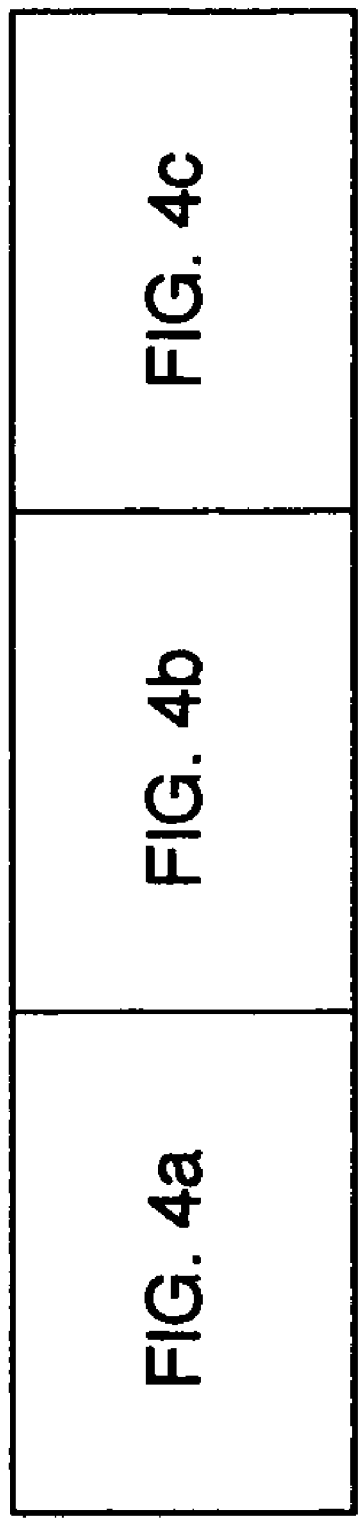
FIG. 3 illustrates the alignment of FIGS. 4a, 4b and 4c.
Figure 4A:
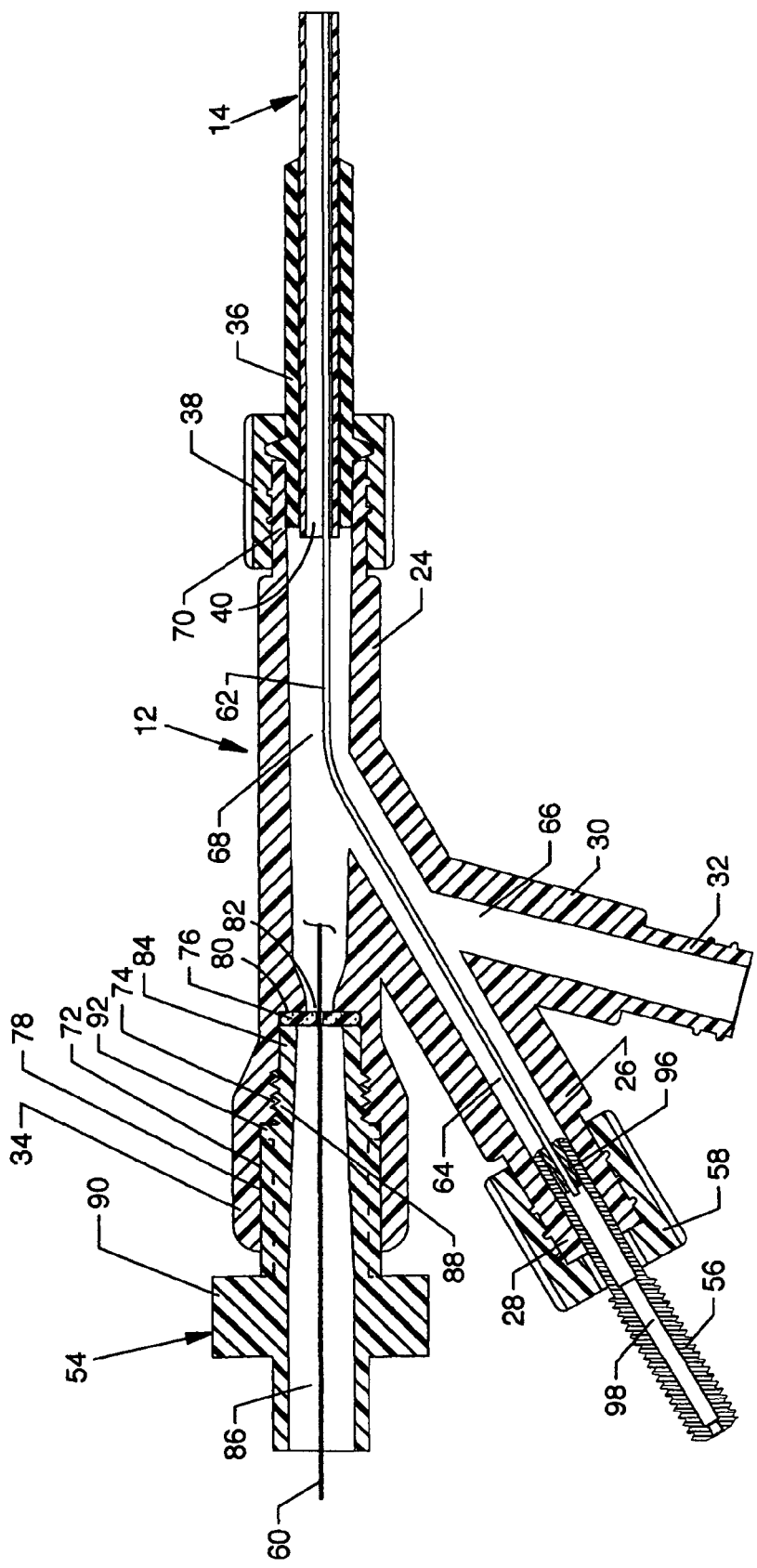
FIGS. 4a, 4b and 4c together illustrate a cross sectional view in different scales of the components of the exhaust-pressure-operated balloon catheter system along the lines 4a-4a, 4b-4b, and 4c-4c of FIG. 1.
Figure 4B:
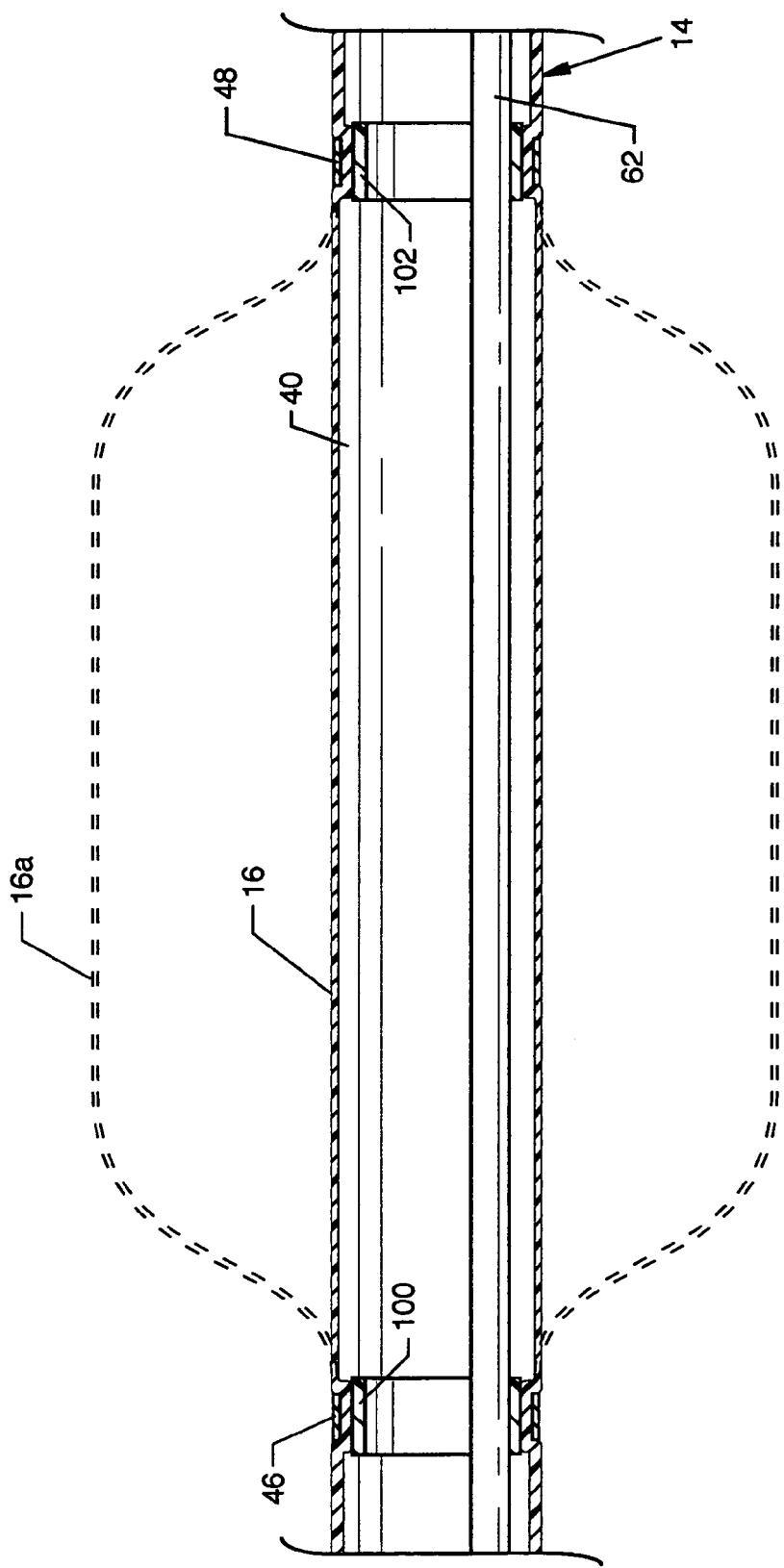
Figure 4C:
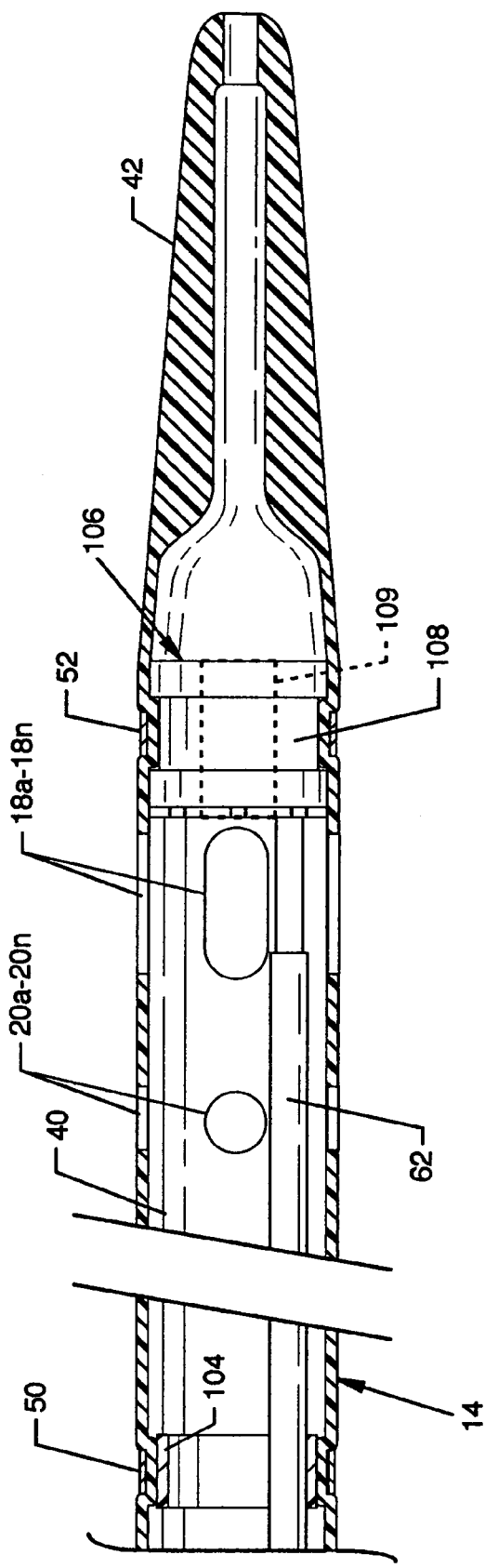

FIG. 2 is a segmented exploded isometric view of the exhaust-pressure-operated balloon catheter system 10, the present invention, and FIGS. 4a, 4b and 4c, the alignment of which is shown in FIG. 3, together illustrate a cross sectional view in different scales of the components of the exhaust-pressure-operated balloon catheter system 10 excluding the full length of the catheter tube 14, but including a guidewire 60 (FIG. 4a) such as is incorporated in the use of the invention. FIGS. 4b and 4c are illustrated in a scale slightly larger than that of FIG. 4a for purposes of clarity. The catheter tube 14, which also serves and functions as an exhaust tube, and a high pressure tube 62 are foreshortened and shown as partial lengths for the purpose of clarity.

With reference to FIG. 2 and FIGS. 4a, 4b and 4c together, the instant invention is further described. The manifold 12 includes connected and communicating passageways and cavities including a high pressure branch passageway 64 within the high pressure branch 26 and integral threaded connector port 28, an exhaust branch passageway 66 within the exhaust branch 30 and integral threaded connector port 32 intersecting and in communication with the high pressure branch passageway 64, and a tapered central passageway 68 extending from and through a distally directed threaded connection port 70 integral to the central tubular body 24 and through the central tubular body 24 to and communicating with a cavity 72, which preferably is cylindrical, located central to the cavity body 34. Internal threads 74 (FIG. 4a) are located about the interior of the cavity body 34 and near the proximal region of the manifold 12 for accommodation of the threaded end of the hemostatic nut assembly 54.

Beneficial to the instant invention is the use of a self-sealing hemostatic valve 76, the shape and functions of which are described in detail in pending application Ser. No. 10/455, 096 entitled "Thrombectomy Catheter Device Having a Self-Sealing Hemostasic Valve" filed on Jun. 05, 2003. The self-sealing hemostatic valve 76 is aligned, captured and housed in the distal portion of the cavity 72 at the proximal region of the manifold 12. The cavity 72 is tubular in shape including a tubular cavity wall 78, the threads 74, and an intersecting planar surface 80 which is annular and circular. An orifice 82 located central to the planar surface 80 is common to the cavity 72 and the tapered central passageway 68. The hemostatic nut assembly 54 includes a passageway 86 extending through the general body and through a cylindrical boss 84 having external threads 88. An integral actuator knob 90 is also part of the hemostatic nut assembly 54. The proximal end of the manifold 12 utilizes the internal threads 74 for attachment of the hemostatic nut assembly 54 to the manifold 12 where the external threads 88 of the hemostatic nut assembly 54 rotatingly engage the internal threads 74 of the manifold 12 to cause the cylindrical boss 84 to bear against the self-sealing hemostatic valve 76, thereby causing the self-sealing hemostatic valve 76 to seal against the guidewire 60 and to seal the proximal portion of the tapered central passageway 68 where such sealing is effective during static or actuated states of the invention. Also included in the hemostatic nut assembly 54 is an annular lip 92, best shown in FIG. 2, which can be utilized for snap engagement with dimples 94 (FIG. 2) protruding inwardly from the tubular cavity wall 78 of the cavity body 34.

Also shown is a ferrule 96 which aligns within the passageway 98 of the threaded high pressure connection port 56 the combination of which aligns within a portion of the high pressure branch passageway 64 at the threaded connector port 28. The proximal end of the high pressure tube 62 is utilized to receive high pressure ablation liquids and suitably secures in a center passage of the ferrule 96 to communicate with the passageway 98 of the threaded high pressure connection port 56. The high pressure tube 62 also extends through the high pressure branch passageway 64, through part of the tapered central passageway 68, through coaxially aligned components including lumen 40 in the catheter tube 14, the connector 38 and the strain relief 36, thence through the balance of the length of the lumen 40 in the catheter tube 14 to attach to other components as now described. The high pressure tube 62 extends through support rings 100, 102 and 104 and to the tip 42 where termination of the high pressure tube 62 is provided in the form of a fluid jet emanator 106, described in other applications and patents assigned to the assignee. The high pressure tube 62 also extends through the radiopaque marker bands 46, 48 and 50 and to the fluid jet emanator 106 and the radiopaque marker band 52. The high pressure tube 62 preferably is attached to the support rings 100, 102 and 104 and the fluid jet emanator 106, such as by welding or other suitable means, where the support rings 100, 102 and 104 and the fluid jet emanator 106 function as co-located supports for the catheter tube 14 in the region beneath the radiopaque marker bands 46, 48, 50 and 52. In FIG. 2, the radiopaque marker bands 46, 48, 50 and 52 are shown displaced distally a short distance from the support rings 100, 102 and 104 and the fluid jet emanator 106 for the purpose of clarity and are shown in frictional engagement in their actual position along and about the distal portion of the catheter tube 14 in FIGS. 4b and 4c.

The relationships of the radiopaque marker bands 46, 48, 50 and 52 and of the support rings 100, 102 and 104 and the fluid jet emanator 106 to each other and to the catheter tube 14 are shown best in FIGS. 4b and 4c. In FIG. 4b, the balloon 16 is shown contiguous with the catheter tube 14, wherein the balloon 16 is of a reduced wall thickness when compared to the general wall thickness of the catheter tube 14. The wall thickness of the balloon 16 is of suitable thickness to allow inflation of the balloon 16 to expand to meet and seal against the wall of the vasculature in which a thrombectomy procedure, drug delivery procedure or other procedure can take place. The radiopaque marker bands 46 and 48 and the support rings 100 and 102 are shown forcibly contacting the full wall thickness of the catheter tube 14 adjacent to the balloon 16, thereby allowing the full length of the thinner wall of the balloon 16 to be utilized for expansion. Alternatively, a suitable portion of the balloon 16 could also be engaged between the radiopaque marker bands 46 and 48 and the support rings 100 and 102. Expansion of the balloon 16 is shown in dashed lines by the expanded balloon 16a.

FIG. 4c shows the positioning of the radiopaque marker bands 50 and 52 around and about the distal portion of the catheter tube 14. The distally located radiopaque marker band 52 is forcibly applied over and about the distal portion of the catheter tube 14 to cause frictional annular engagement of a portion of the catheter tube 14 with all or part of an annular groove 108 of the fluid jet emanator 106. Such frictional engagement is sufficient to place the outer radius surface of the radiopaque marker band 52 (also 46, 48 and 50) in a position lesser than the general and greater outer radial surface of the catheter tube 14, thereby providing, in part, catheter tube 14 having no elements protruding beyond the general outer radial surface thereof for unimpeded and smooth distal or proximal transition of the catheter tube 14 within a vein, artery or the like. A passage 109 is shown central to the fluid jet emanator 106 to accommodate passage of a guidewire.

Structure is provided to nurture and aid introduction of and passage of the distal portion of the catheter tube 14 through blood vessels, arteries and the like to the sites of thrombotic deposits or lesions. The tapered tip 42, as opposed to a rounded and non-tapered tip, can part and more easily penetrate thrombotic deposits or lesions during insertional travel in a distal direction instead of advancing or pushing such thrombotic deposits or lesions distally. The decreasing diameter in a distal direction of the tapered tip 42 also allows for increasing flexibility to negotiate and pass through tortuous paths.

The exhaust tube support rings 100 and 102 in use with the radiopaque marker bands 46 and 48 in the regions surrounding the opposed ends of the balloon 16 are examples of structures offering support or reinforcement along the catheter tube 14 in the regions surrounding the ends of the balloon 16. The exhaust tube support ring 104 and fluid jet emanator 106, in use with the radiopaque marker bands 50 and 52, are other examples of structures offering support or reinforcement along the catheter tube 14. Such support allows the use of thinner wall dimension for the catheter tube 14 to allow for a larger and more effective and efficiently sized lumen 40, as well as contributing to a reduced size outer diameter. Such support also contributes to supportively maintaining the diameter and overall shape of the catheter tube 14 when the catheter tube 14 is pushed or advanced along a vein or vessel, as well as aiding torsional support.

Mode of Operation

Generally, a normal guidewire is deployed in a vessel requiring treatment, or in the alternative, a filter guidewire or balloon occlusion guidewire could be used. After other necessary interventional procedures, the exhaust-pressure-operated balloon catheter system 10 is advanced over the guidewire for debris/thrombus removal, drug infusion or other procedures and maneuvered into the appropriate position for treatment. A guide catheter or sheath can be incorporated as necessary to offer assistance in placing the catheter tube 14 of the exhaust-pressure-operated balloon catheter system 10 within the desired location of the vasculature. The exhaust-pressure-operated balloon catheter system 10 is activated, wherein the balloon 16 is automatically and expandingly deployed forming an expanded balloon 16a and debris or drugs are removed or infused. The balloon 16 can be alternately pressurized and depressurized, wherein the exhaust-pressure-operated balloon catheter system 10 may be moved proximally or distally during the procedure to maximize the effect of the system. When the procedure is complete, the balloon 16 generally is deflated sufficiently under normal arterial pressure to be removed safely, or deflation can be aided with a manual syringe attached to an effluent line, or deflation could be aided via use of a roller pump. Further interventions can be executed as normal over the remaining wire or wire device.

Figure 5:
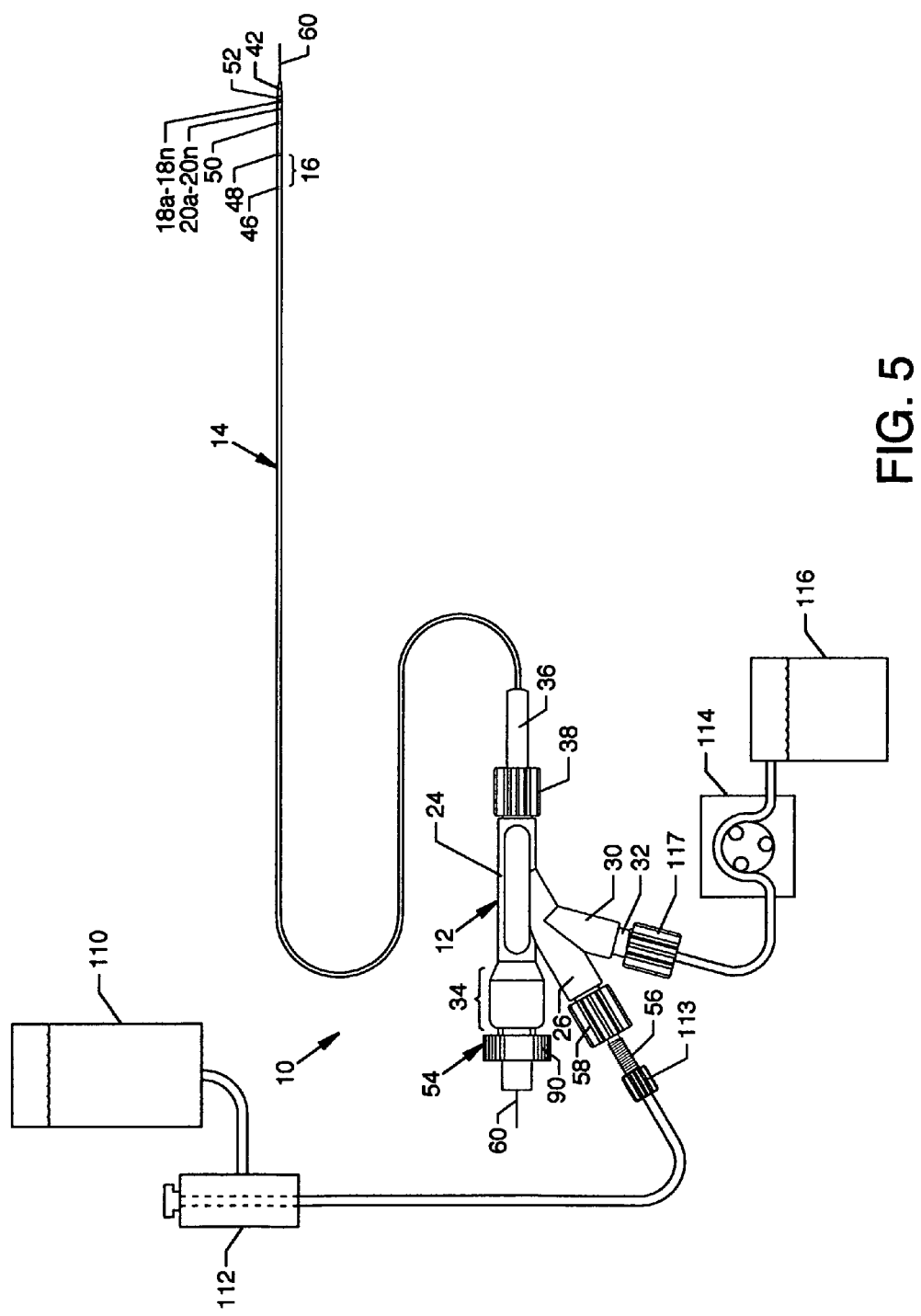
FIG. 5 illustrates the invention connected to ancillary devices.
Figure 6:
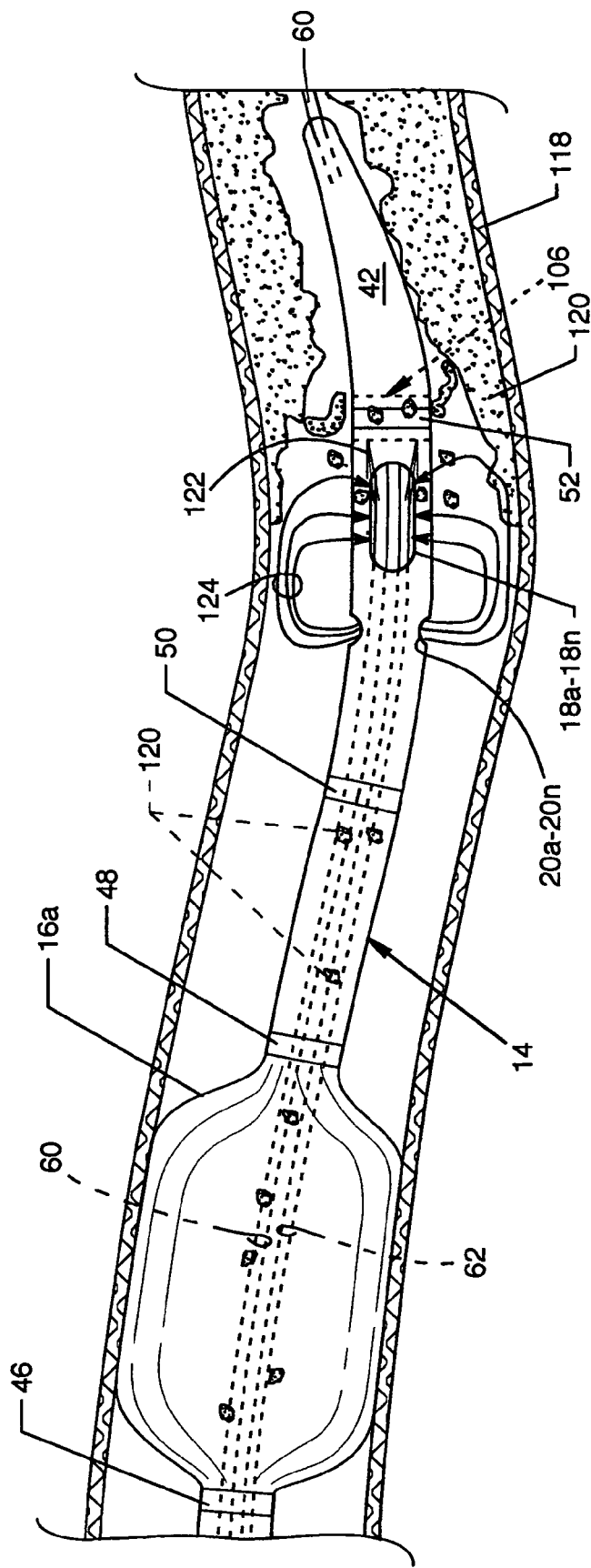
FIG. 6 illustrates the exhaust-pressure-operated balloon catheter system in the performance of the method of use of the present invention.

More specifically, FIGS. 5 and 6 illustrate the mode of operation where FIG. 5 illustrates the invention connected to ancillary devices, and where FIG. 6 illustrates the distal portion of the exhaust-pressure-operated balloon catheter system 10 in the performance of the method of use of the present invention. The mode of operation is best understood by referring to FIGS. 5 and 6 along with previously described figures.

The exhaust-pressure-operated balloon catheter system 10 is shown engaged over and about a guidewire 60, wherein the guidewire 60 (previously engaged into a vein or artery) first slidably engages the lumen 40 of the guidewire tube 14 at the tapered tip 42 followed by slidable engagement of the passage 109 of the fluid jet emanator 106, slidable engagement of the tapered central passageway 68, and slidable and sealed engagement with the hemostatic valve 76 to exit from the hemostatic nut assembly 54. A high pressure fluid source 110 and a high pressure fluid pump 112 connect to the manifold 12 via the threaded high pressure connection port 56 and a connector 113. An exhaust regulator 114, such as a roller pump or other suitable device, and a collection chamber 116 connect to the threaded connector port 32 of the exhaust branch 30 by a connector 117, as shown.

FIG. 6 illustrates the exhaust-pressure-operated balloon catheter system 10 in the performance of the method of use of the present invention, with particular attention to the distal portion of the exhaust tube 14 including the flexible tapered tip 42 positioned in a blood vessel 118, artery or the like at the site of a thrombotic deposit or lesion 120 where the blood vessel 118 and the main thrombotic deposit or lesion 120 are shown in cross section. Multiple jet streams of high velocity jet flow 122 of saline (or other suitable fluid) are emitted in a proximal direction from the fluid jet emanator 106 to impinge upon and carry away thrombotic deposits or lesions 120 which have been reduced to particulate form. Alternatively, other fluid jet emanators of different structures can be incorporated within the distal portion of the catheter tube 14 as an alternative to the jet emanator 106 illustrated in this figure to emanate or emit one or more high velocity jet flow(s) 122 proximally along or near the longitudinal axis of the catheter tube 14 to accomplish the same purpose as that described for the fluid jet emanator 106. The high velocity jet flow(s) 122 of saline pass outwardly through the outflow orifice(s) 20a-20n in a radial direction creating cross stream jet(s) 124 directed outwardly toward the wall of the blood vessel 118 and are influenced by the low pressure at the inflow orifice(s) 18a-18n to cause the cross stream jet(s) 124 to flow distally and circumferentially to impinge on, provide drag forces on, and break up thrombotic deposits or lesions 120 and to, by entrainment, urge and carry along the particles of thrombotic deposits or lesions 120 through the inflow orifice(s) 18a-18n, a relatively low pressure region, into the high velocity jet flows 122 where the thrombus 120 is further macerated into microscopic particles, and thence into the catheter tube lumen 40 to pass through the expanded balloon 16a, and thence further through the lumen 40 for subsequent exhausting. The exhaust outflow is driven by internal pressure which is created by the high velocity jet flow(s) 122 and the fluid entrained through the inflow orifice(s) 18a-18n to cause pressurization of the lumen 40 and the balloon 16 and is utilized to several advantages. One advantage of which is that in a no flow situation when distal flow of blood is stopped by inflation of the intervening inflated and expanded balloon 16a, the particles of thrombotic deposits or lesions 120 are substantially trapped and can be more effectively circulated, recirculated and rediluted until all that remains is saline and minute particles of thrombotic deposits or lesions 120 which are subsequently removed in a proximal direction through the lumen 40 of the catheter tube 14 by promoting flow through the exhaust regulator 114. Another advantage is the utilization of the exhaust outflow and internal pressure which is created by the high velocity jet flow(s) 122 in combination with the restriction of the outflow, such as influenced by the exhaust regulator 114, to cause automatic expansion of the balloon 16 which forcibly impinges and seals against the inner walls of the blood vessel 118. The reduced thickness of the material comprising the balloon 16 allows the balloon 16 to expand sufficiently to become an expanded balloon 16a restricted by impingement with the wall of the blood vessel 118. Inflation pressure and flows can be influenced by controlling of input pressure fluid at the high pressure fluid pump 112 and by controlling of the exhaust rate at the exhaust regulator 114. The present invention discloses an exhaust-pressure-operated balloon catheter system 10 utilizing the concept of a continuously formed inflatable and expandable balloon being continuously formed of the same material as the catheter (exhaust tube) and automatically inflated by internal pressurization as caused by high velocity jet flows, cross stream jets, and the like. Such a concept can also be applied to other thrombectomy catheters and systems, such as, but not limited to, all AngioJet® catheters including rapid exchange catheters, over-the-wire catheters, and catheters which are pressurized by a fluid flow source.

Various modifications can be made to the present invention without departing from the apparent scope thereof.

| EXHAUST-PRESSURE-OPERATED BALLOON CATHETER SYSTEM PARTS LIST | |
|---|---|
| 10 | exhaust-pressure-operated balloon catheter system |
| 12 | manifold |
| 14 | catheter tube |
| 16 | balloon |

-continued

EXHAUST-PRESSURE-OPERATED BALLOON CATHETER SYSTEM PARTS LIST

| | |
|---|---|
| 16a | expanded balloon |
| 18a-n | inflow orifices |
| 20a-n | outflow orifices |
| 24 | central tubular body |
| 26 | high pressure branch |
| 28 | threaded connector port |
| 30 | exhaust branch |
| 32 | threaded connector port |
| 34 | cavity body |
| 36 | strain relief |
| 38 | connector |
| 40 | lumen |
| 42 | tapered tip |
| 46 | radiopaque marker band |
| 48 | radiopaque marker band |
| 50 | radiopaque marker band |
| 52 | radiopaque marker band |
| 54 | hemostatic nut assembly |
| 56 | threaded high pressure connection port |
| 58 | connector |
| 60 | guidewire |
| 62 | high pressure tube |
| 64 | high pressure branch passageway |
| 66 | exhaust branch passageway |
| 68 | tapered central passageway |
| 70 | threaded connection port |
| 72 | cavity |
| 74 | internal threads |
| 76 | self-sealing hemostatic valve |
| 78 | tubular cavity wall |
| 80 | planar surface |
| 82 | orifice |
| 84 | boss |
| 86 | passageway |
| 88 | external threads |
| 90 | actuator knob |
| 92 | annular lip |
| 94 | dimple |
| 96 | ferrule |
| 98 | passageway |
| 100 | support ring |
| 102 | support ring |
| 104 | support ring |
| 106 | fluid jet emanator |
| 108 | annular groove |
| 109 | passage |
| 110 | high pressure fluid source |
| 112 | high pressure fluid pump |
| 113 | connector |
| 114 | exhaust regulator |
| 116 | collection chamber |
| 117 | connector |
| 118 | blood vessel |
| 120 | thrombotic deposit or lesion |
| 122 | high velocity jet flow |
| 124 | cross stream jets |

It is claimed:

1. An exhaust-pressure-operated balloon catheter thrombectomy system for use within a vessel comprising:
  a. a manifold including:
    (1) a central tubular body;
    (2) a high pressure branch including an integral threaded connector port extending angularly from the central tubular body;
    (3) an exhaust branch including an integral threaded connector port extending angularly from the high pressure branch; and,
    (4) a cavity body, having a hemostatic nut assembly, extending proximally from the central tubular body;
  b. a catheter tube formed from a first material, including an exhaust lumen, extending distally from the manifold through a strain relief and toward a distally located tapered tip;
  c. a plurality of outflow and inflow orifices on the catheter tube and in communication with the exhaust lumen in close proximity to the tapered tip;
  d. a high pressure tube connectively extending from the high pressure branch, through the manifold and through the catheter tube to a fluid jet emanator located distal to the plurality of outflow and inflow orifices, and a fluid distally carried under high pressure from the manifold to the fluid jet emanator;
  e. an inflatable thin walled section balloon formed from the first material of the catheter tube and aligned between two sections of full wall catheter tube proximal to the plurality of outflow and inflow orifices, where the outflow and inflow orifices are between the fluid jet emanator and the thin walled section balloon, and the outflow and inflow orifices are in communication with the thin walled section balloon and the emanator through the exhaust lumen; and
  f. the exhaust lumen of the catheter tube communicating with the thin walled section balloon, the exhaust lumen and thin walled section balloon of the catheter tube being sustainably pressurized by a proximal exhaust flow of the fluid from the fluid jet emanator and an entrained fluid from the inflow and outflow orifices, the proximal exhaust flow crossing the inflow and outflow orifices between the emanator and the thin walled section balloon and combining with the entrained fluid, and the proximal exhaust flow including the fluid from the fluid jet emanator and the entrained fluid inflating the thin walled section balloon into an expanded configuration.

2. The exhaust-pressure-operated balloon catheter system of claim 1, further including opposed radiopaque marker bands distal and proximal of the thin walled section balloon.

3. The exhaust-pressure-operated balloon catheter system of claim 2, further including support rings adjacent to the thin walled section balloon.

4. The exhaust-pressure-operated balloon catheter system of claim 1, wherein the hemostatic nut assembly engages the cavity body.

5. The exhaust-pressure-operated balloon catheter system of claim 4, wherein the cavity body includes dimples protruding inwardly on the cavity body for engagement with an annular lip on the hemostatic nut assembly.

6. The exhaust-pressure-operated balloon catheter system of claim 1, wherein the thin walled section balloon is deployable and expandable about a distal region of the catheter tube to act as an occlusive device when an exhaust pressure control device is operated.

7. The exhaust-pressure-operated balloon catheter system of claim 1, wherein the fluid jet emanator and inflow and outflow orifices define a location for ablative cross stream flows generated by the fluid from the fluid jet emanator, and wherein the thin walled section balloon is located proximal to the location of such ablative cross stream flows.

8. The exhaust-pressure-operated balloon catheter system of claim 1, wherein the exhaust branch of the manifold includes an exhaust regulator, and the exhaust regulator is configured to cooperate with the proximal exhaust flow to control inflation pressure at the thin walled section balloon.

9. A method of occluding a location in vasculature comprising:
  a. providing an exhaust-pressure-operated balloon catheter including:
    a manifold comprising a high pressure branch having a high pressure connector, and an exhaust branch,
    a full wall catheter tube formed from a first material and having an exhaust lumen, the catheter tube extending distally from the manifold, and the catheter tube includes inflow and outflow orifices in communication with the exhaust lumen, a high pressure tube communicating with the high pressure connector and extending through the manifold and through the catheter tube to a fluid jet emanator, and a fluid distally carried under high pressure from the manifold to the fluid jet emanator, an integral, flexible, expandable, and inflatable thin wall section balloon aligned between two sections of the full wall catheter tube, the outflow and inflow orifices are between the fluid jet emanator and the expandable balloon, and the outflow and inflow orifices are in communication with the expandable balloon and the emanator through the exhaust lumen;

b. positioning the balloon at the location in the vasculature; and c. sustainably inflating the balloon into an expanded configuration by supplying high pressure flow to a fluid jet emanator and restricting the exhaust outflow, wherein sustainably inflating the balloon includes:

directing the high pressure flow proximally through the fluid jet emanator and across one or more of inflow and outflow orifices, the one or more inflow and outflow orifices are between and in communication with the balloon and the fluid jet emanator, entraining and combining fluid from the one or more of inflow and outflow orifices with the proximal high pressure flow as a proximal exhaust flow, and delivering the proximal exhaust flow to the balloon for sustainable inflation.

10. The method of claim 9, wherein the exhaust-pressure-operated balloon catheter includes the one or more inflow and outflow orifices situated distally from the balloon, and further comprising:

generating a cross stream ablative jet.

11. The method of claim 10, further comprising:
stopping the cross stream ablative jet and deflating the balloon.

12. The method of claim 11, further comprising:
repositioning the deflated balloon at another location in the vasculature; and,
reinflating the balloon by resupplying high pressure flow and re-restricting the exhaust outflow and generating another cross stream ablative jet.

13. An exhaust-pressure-operated balloon catheter thrombectomy system comprising:

a. a manifold comprising a high pressure branch having a high pressure connector, and an exhaust branch;

b. a catheter tube formed from a first material and having an exhaust lumen, the catheter tube extending distally from the manifold, and the catheter tube includes inflow and outflow orifices in communication with the exhaust lumen;

c. a high pressure tube communicating with the high pressure connector and extending through the manifold and through the catheter tube to a fluid jet emanator, and a fluid distally carried under high pressure from the manifold to the fluid jet emanator;

d. a thin walled section formed from the first material of the catheter tube located between two sections of thicker walled catheter tube formed from the first material, where the thin walled section is an expandable balloon, the outflow and inflow orifices are between the fluid jet emanator and the expandable balloon, and the outflow and inflow orifices are in communication with the expandable balloon and the emanator through the exhaust lumen; and e. the exhaust lumen of the catheter tube communicating with the expandable balloon, the exhaust lumen of the catheter tube being sustainably pressurized by a proximal exhaust flow of the fluid from the fluid jet emanator and an entrained fluid from the inflow and outflow orifices, the proximal exhaust flow crossing the inflow and outflow orifices between the emanator and the expandable balloon and combining with the entrained fluid, and the proximal exhaust flow including the fluid from the fluid jet emanator and the entrained fluid sustainably inflating the expandable balloon into an expanded configuration.

14. The exhaust-pressure-operated balloon catheter system of claim 13, further comprising an exhaust regulator.

15. The exhaust-pressure-operated balloon catheter system of claim 14, wherein the exhaust regulator is in the exhaust branch, and the exhaust regulator is configured to cooperate with the proximal exhaust flow to control inflation pressure at the thin walled section balloon.

16. An exhaust-pressure-operated balloon catheter system comprising:

a. a manifold comprising a high pressure branch having a high pressure connector, and an exhaust branch;

b. a catheter tube formed from a first material and having an exhaust lumen, the catheter tube extending distally from the manifold, and the catheter tube includes inflow and outflow orifices in communication with the exhaust lumen;

c. a high pressure tube communicating with the high pressure connector and extending through the manifold and through the catheter tube to a fluid jet emanator, and a fluid distally carried under high pressure from the manifold to the fluid jet emanator;

d. an expandable balloon, the outflow and inflow orifices are between the fluid jet emanator and the expandable balloon, and the outflow and inflow orifices are in communication with the expandable balloon and the emanator through the exhaust lumen; and e. the exhaust lumen of the catheter tube communicating with the expandable balloon, the exhaust lumen of the catheter tube configured for sustainably pressurizing by a proximal exhaust flow along a composite exhaust path extending from the fluid jet emanator to the expandable balloon, the composite exhaust path configured to receive fluid from the fluid jet emanator and an entrained fluid from the inflow and outflow orifices to form the proximal exhaust flow, the composite exhaust path extends through the inflow and outflow orifices between the emanator and the expandable balloon, the proximal exhaust flow in the composite exhaust path is configured to sustainably inflate the expandable balloon into an expanded configuration.

17. The exhaust-pressure-operated balloon catheter system of claim 16, wherein the expandable balloon is deployable and expandable about a distal region of the catheter tube to act as an occlusive device when an exhaust pressure control device is operated.

18. The exhaust-pressure-operated balloon catheter system of claim 16, wherein the exhaust branch of the manifold includes an exhaust regulator, and the exhaust regulator is configured to cooperate with the proximal exhaust flow to control inflation pressure at the expandable balloon.

19. The exhaust-pressure-operated balloon catheter system of claim 16, wherein the fluid jet emanator and inflow and outflow orifices define a location for ablative cross stream flows generated by the fluid from the fluid jet emanator, and wherein the expandable balloon is located proximal to the location of such ablative cross stream flows.

* * * * *

UNITED STATES PATENT AND TRADEMARK OFFICE
CERTIFICATE OF CORRECTION

PATENT NO.         : 8,162,878 B2                                         Page 1 of 1
APPLICATION NO.    : 11/294006
DATED              : April 24, 2012
INVENTOR(S)        : Bonnette et al.

It is certified that error appears in the above-identified patent and that said Letters Patent is hereby corrected as shown below:

IN THE CLAIMS

In Column 11, Lines 39-41, Claim 12 delete "reinflating the balloon by resupplying high pressure flow and re-restricting the exhaust outflow and generating another cross stream ablative jet" and insert -- reinflating the balloon by resupplying the high pressure flow and re-restricting the exhaust outflow and generating a second cross stream ablative jet --, therefor.

In Column 11, Lines 56-57, Claim 13, delete "tube formed from the first material, where the thin wall section" and insert -- tube formed from the first material, wherein the thin walled section --, therefor.

In Column 12, Line 38, Claim 16, delete "configured for sustainably pressurizing by" and insert -- configured to be sustainably pressurized by --, therefor.

Signed and Sealed this
Thirtieth Day of April, 2013

Teresa Stanek Rea
*Acting Director of the United States Patent and Trademark Office*